United States Patent [19]

Isakov et al.

[11] 4,215,694

[45] Aug. 5, 1980

[54] LASER THERAPY APPARATUS

[76] Inventors: Viktor L. Isakov, ulitsa Fedorova, 1, kv. 67; Yan Y. Popov, ulitsa Yakira, 16/18, korpus 2, kv. 70; Tsaly I. Vaisberg, ulitsa Engelsa, 7/10, kv. 24; Rostislav A. Kharzhevsky, prospekt 40-letia Oktyabrya, 100/2, kv. 39; Vladimir M. Pshenichny, ulitsa Parkhomenko, 60, kv. 98; Andrei I. Koba, ulitsa O. Vishni, 9, kv. 35; Boris G. Khlyvnjuk, ulitsa Moskovskaya, 5, kv. 38; Nikolai N. Solomko, ulitsa Zhadanovskogo, 4, kv. 6, all of Kiev, U.S.S.R.; Ivan V. Kudryavtsev, deceased, late of Kiev, U.S.S.R.; by Galina A. Kudryavtseva, administrator, ulitsa Suvorova, 13, kv. 108, Kiev, U.S.S.R.

[21] Appl. No.: 911,673

[22] Filed: Jun. 1, 1978

Related U.S. Application Data

[63] Continuation of Ser. No. 686,482, May 14, 1976, abandoned.

[51] Int. Cl.$^2$ ............................................. A61N 5/01
[52] U.S. Cl. ..................... 128/303.1; 331/DIG. 1; 33/1 M; 250/202; 219/121 L; 356/375; 356/399
[58] Field of Search ............... 128/303.1, 303 B, 395, 128/2 S; 331/DIG. 1; 33/1 M; 250/202 R, 203 R; 219/121 L, 121 LM; 356/373, 375, 399, 400

[56] References Cited

U.S. PATENT DOCUMENTS

| | | | |
|---|---|---|---|
| 3,338,235 | 8/1967 | Gordon | 128/303 B |
| 3,474,248 | 10/1969 | Brown et al. | 331/DIG. 1 |
| 3,673,412 | 6/1972 | Olson | 250/202 R |
| 3,766,355 | 10/1973 | Kottkamp | 250/202 R |
| 4,069,823 | 1/1978 | Isakov et al. | 128/303.1 |

OTHER PUBLICATIONS

Goldman, "Biomedical Aspects of the Laser," Springer-Verlag, New York Inc., 1967.
Goldman et al., "Laser Systems and their Applications in Medicine and Biology," Advances in Biomedical Engineering and Medical Physics, vol. 1, pp. 317-321.

*Primary Examiner*—Henry J. Recla
*Attorney, Agent, or Firm*—Lackenbach, Lilling & Siegel

[57] ABSTRACT

A laser therapy apparatus comprising a radiating source, a control system of said radiating source, which system is connected to said source, a mechanical beam shifting scanner connected to said radiating source, a unit for processing and storing information on a program of exposing biological objects to irradiation, to whose output there is connected a unit control for reading out information from said information processing and storage unit, as well as an electromechanical unit whose outputs are connected to the mechanical beam shifting scanner, said electromechanical unit having a drive by means of which directional irradiation, i.e. the beam, is focused on an object exposed to irradiation and oriented in three spatial coordinates, one output of the control and information readout unit being connected to the input of the electromechanical unit, whereas its second output is connected to the input of the radiating source control system.

8 Claims, 12 Drawing Figures

LASER THERAPY APPARATUS

This application is a continuation application of applicants' Ser. No. 686,482, filed on May 14, 1976 of Viktor Leonidovich Isakov, et al. for "LASER THERAPY APPARATUS", now abandoned.

The present invention relates to medical equipment and, more particularly, to laser therapy apparatus for clinical radiotherapy, for example, for treating malignant and benign surface tumors by exposing them to laser irradiation and for carrying out medicobiological tests of biological objects.

This far, the most advanced and closest in its technical characteristics to the proposed apparatus is the one described in the book by L. Goldman, "Biomedical Aspects of the Laser", New York, 1976, Springer-Verlag.

The above-mentioned apparatus comprises a radiating source whose function is performed by a laser, a laser control system, and devices for shifting and focusing the laser beam, i.e. scanning systems.

A scanning system includes two movable platforms upon one of which there is mounted a radiating head. Mounted on said radiating head, on the side of its output end, is a focusing barrel.

The platforms are adapted for motion in the horizontal plane along two mutually perpendicular guides attached to the ceiling of an operating room.

The radiating head and its platform are provided with a suspension means which makes it possible for said platform to move in the vertical direction as well.

High-voltage power units of the laser are accommodated in separate premises.

In order to direct the laser beam at an object of exposure, the radiating head must be displaced in the horizontal and vertical planes so as to bring the laser beam home to a predetermined point of the operative field. The beam is then focused as required with the aid of the focusing barrel.

In the apparatus under review, all operations involved in directing the laser beam at an object are performed manually. Furthermore, no provision is made in this type of apparatus for remote control means for directing and focusing the laser beam; no provision is made for programmed operation of the laser and scanning system in the automatic mode. The foregoing factors make it practically impossible to expose large areas of a tumor to irradiation.

The apparatus in question is not provided with means for spatially correcting the location of the laser beam in case of an accidental shift of an object exposed to irradiation in the course of an operation, which may lead to exposure of healthy tissues.

Finally, the apparatus under review lacks means for monitoring and representing the beam movement.

It is an object of the present invention to provide a laser therapy apparatus which would rule out any change or failure in exposing some areas of a tumor to irradiation.

It is another object of the invention to raise the accuracy of directing the beam at areas of exposure.

It is still another object of the invention to cut down the operating time.

It is yet another object of the invention to provide a laser therapy apparatus with means for spatially correcting the laser beam location in case of a substantial displacement of an object in the course of programmed irradiation.

Additionally, it is an object of the present invention to provide means for monitoring the location of the laser beam and graphically representing the beam movement.

The foregoing objects of the invention are attained by providing a laser therapy apparatus comprising a radiating source, a control system of said radiating source, which is connected to said source, and a mechanical beam shifting scanner connected to said radiating source, which device further includes, in accordance with the invention, a unit for processing and storing information on a program of irradiating biological objects, to whose output there is connected a control unit for reading out information from the information processing and storage unit, and an electromechanical unit whose outputs are connected to the mechanical beam shifting scanner, said electromechanical unit having a drive to focus the directional irradiation, i.e. the beam on an object to be exposed to irradiation and orient it in three spatial coordinates, one output of the information readout and control unit being connected to the input of the electromechanical unit, whereas its second output is connected to the input of the control system of the radiating source.

The information processing and storage unit can include an information input unit whose output is connected to a first input of a code storage register whose output is connected to a tape puncher for punching tape that serves as an irradiation data strorage means, an output of the tape puncher being connected to a second input of the code storage register.

The drive of the electromechanical unit may comprise three step electromotors, the first and second being intended to shift the beam in the horizontal plane in mutually prependicular directions, whereas the third motor is intended to shift the beam in the vertical direction, i.e. to focus it. Mounted on the shaft of each of said motors is a step counter.

The control and information readout unit may comprise a punch-tape reader whose outputs are connected to first inputs of the step counter and the register; connected to a second input of the step counter is a first OR circuit whose first, second and third inputs are respectively connected to the first, second and third step counters of the step electromotors of the electromechanical unit; the control and information readout unit further includes a first decoder whose input is connected to the output of the step counter, its output being connected to a second input of the register whose first input is coupled via a second OR circuit to the reader; connected to a third input of the register is a third OR circuit whose first input is connected to a third input of the step counter and a first output of a control board; second inputs of the second and third OR circuits are connected to the system for controlling the radiating source; a third input of the second OR circuit is connected to a second output of the control board whose third output is connected to an input of a pulse generator; the control and information readout unit still further includes a second decoder whose first input is connected to a second output of the register, its second input being connected to a fourth output of the control board; the control and information readout unit then includes a first AND circuit whose first input is connected to a first output of the second decoder, a second input of said AND circuit being connected to an output of the pulse generator, whereas the output of said AND circuit is connected to an input of a first commutator whose output is connected to an input of a first amplifier, the latter's output being connected to windings of the first step motor of the electromechanical unit; the control and information readout unit also includes a second AND circuit whose first input is connected to a second output of the second decoder, whereas its second input is connected to the output of the pulse generator, the output of said second AND circuit being connected to an input of a second commutator whose output is connected to an input of a second amplifier whose output is connected to windings of the second step motor of the electromechanical unit; the control and information readout unit then incorporates third AND circuit, its second input being connected to the output of the pulse generator, its first output being connected to the third output of the second decoder, its output being connected to an input of a third commutator whose output is connected to an input of a third amplifier, the latter's output being connected to windings of the third step motor of the electromechanical unit; then, the control and information readout unit includes a fourth AND circuit whose first input is connected to a fourth output of the second decoder, whereas a second input and an output of said fourth AND circuit, as well as a fifth output of the second decoder are connected to the control system of the radiating source.

It is also expedient that the proposed apparatus should include a device for following the location of an object exposed to irradiation connected to the control and information readout unit. This device is to include a pulse generator whose output is connected to position sensors whose outputs are connected to the inputs of the register whose first and second outputs are respectively connected to the third input of the fourth AND circuit and the third input of the second decoder of the control and information readout unit, each third and fourth output of the register being respectively connected to the first inputs of the first and second AND circuits whose second inputs are connected to the pulse generator of the control and information readout unit, the outputs of said circuits being connected to an input of an electronic commutator which is coupled via an amplifer to a step motor to rotate a holder of said position sensors; installed in each said holder coaxially with the latter is a movable disc with ferrite inserts, which disc is coupled by means of a rack-and-pinion gear and with carriages moving in longitudinal and transverse directions respectively to a telescopic probe mounted on one of the carriages, the opposite end of said probe being attached to the irradiation object.

It is preferable that the apparatus of the present invention should be provided with a graph plotter connected to the control and information readout unit and comprising two step electromotors respectively coupled by means of reduction gears and via carriages to a movable table over which there is mounted an electromagnet-controlled pen controlled from the control board.

It is practicable that the apparatus should also be provided with a unit for simulating operating conditions of the radiating source. This unit must comprise a time relay whose first output is connected to a first input of an AND circuit whose output is connected to an input of a pulse forming circuit; the input of the time relay and first and second inputs of the AND circuit, as well as the first output of the pulse forming circuit are respectively connected to the fifth output of the second decoder, the second input of the fourth AND circuit, the output of this circuit, and the second inputs of the second and third OR circuits of the control and information readout unit; second outputs of the time relay and the pulse forming circuit are respectively connected to a pumping indicator and an ignition indicator.

In the apparatus of the present invention, the function of the information processing and storage unit and control and information readout unit may be performed by a photomask readout device and a photomask control unit whose input is connected to an output of the photomask readout device comprising two step electromotors coupled through reduction gears to carriages which move a movable table, whereupon the photomask is placed, in two mutually perpendicular directions; use is also made of a luminous flux source, a photosensitive element and four limit switches; the photomask control unit comprises a counter whose first input is connected to the control board and the first input of the first OR circuit, the counter's second input being connected to the output of the second OR circuit, the second input of the first OR circuit being connected to the control system of the radiating source, whereas the output of said system is connected to an input of a flip-flop whose second input is connected to the output of the first AND circuit and the control system of the radiating source, the flip-flop's output being connected to a first input of a decoder whose second input is connected to the output of the counter, the first inputs of the first, second and third AND circuits being connected to the output of the pulse former whose input is connected to the photosensitive element of the photomask readout device, the outputs of the second and third AND circuits being connected to the inputs of the second OR circuit; there is also a NOR circuit whose first input is connected to the second input of the second AND circuit and the first limit switch of the photomask readout device, a second input of this circuit being connected to the second limit switch and the second input of the third AND circuit, its third input being connected to the third limit switch, whereas its fourth input is connected to the output of the control board and the fourth limit switch, the output of the NOR circuit being connected to the second output of the first AND circuit whose third input is connected to the control system of the radiating source, the first output of the decoder is connected to the first output of the fourth AND circuit, its second output being connected to the first input of the fifth AND circuit; the second inputs of the fourth AND circuit and fifth AND circuit and fifth are connected to the first output of the register of the device for following the irradiation object location; the third inputs of these circuits are connected to the pulse generator output, each output of the fourth and fifth AND circuits is connected to the electronic commutator, which output is coupled via are amplifier to a step motor of the electromechanical unit of the mechanical scanner and to a step motor of the photomask readout device.

The apparatus of the present invention effectively meets all the requirements imposed on it and may find extensive application in different fields of medicine.

For example, the apparatus can be used in oncology for local necrotization of tumoral nodes by laser irradiation. It can be employed in surgery for dissection of tissues by a continuous-action laser beam. The apparatus is also applicable in dermatology for selective sparin destruction by laser irradiation of appropriately stained pathological formations. The apparatus is useful in medicobiological experiments aimed at studying the effects of pulsed and continous laser beam on cell preparations, normal tissues and organs of experimental animals, tumors induced in such animals, etc.

In addition, the apparatus is applicable in therapy for treating burns and for light massage. It is also an effective tool in acupuncture, whereby use is made of a HeNe laser beam. The invention can be employed in ultrasonic therapy, radiotherapy and roentgenotherapy for sparing irradiation of affected tissues of internal organs according to a program based on comprehensive diagnostic data. Finally, the proposed apparatus may be useful in some operations involved in the manufacture of surgical and stomatologic prostheses.

Other objects and advantages of the present invention will become more apparent from the following detailed description of a preferred embodiment thereof taken in conjunction with the accompanying drawings, wherein.

Figure 1:
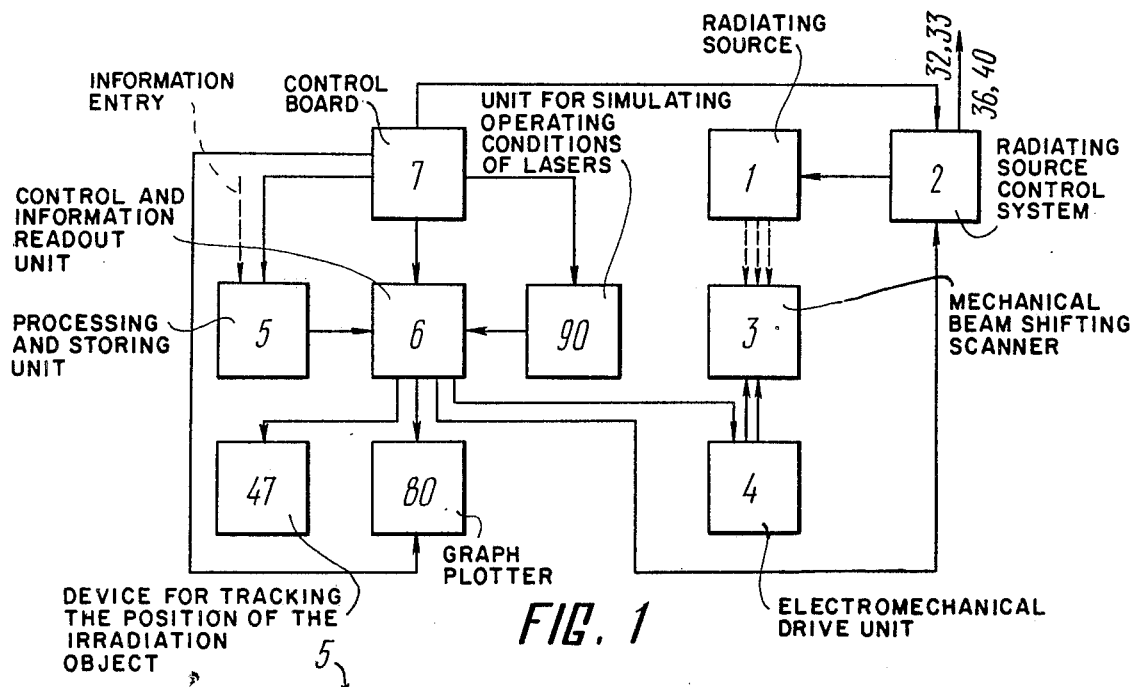
FIG. 1 is a general block diagram of an apparatus in accordance with the invention.

Referring now to FIG. 1, the proposed laser therapy apparatus comprises a radiating source 1, to which there are connected a system 2 for controlling said radiating source 1 and a mechanical beam shifting scanner 3 with an electromechanical unit 4 having a drive (not shown) by means of which directional irradiation, i.e. the beam, is focused on an object to be exposed to irradiation and oriented in three coordinates.

The apparatus further includes a unit 5 for processing and storing information on a program of irradiation of biological objects, to which there is connected a unit control 6 for reading out information transferred from the information processing and storage unit 5. One output of the control and information readout unit 6 is connected to an input of the electromechanical unit 4, whereas a second output of said unit 6 is connected to an input of the control system 2 of the radiating source 1.

In the proposed apparatus, the function of the radiating source may be performed by one or several lasers.

The apparatus further includes a control board 7, each of whose outputs is respectively connected to an input of the information processing and storage unit 5, and the control and information readout unit 6 with the control system 2 of the radiating source 1. Information on irradiation is entered at a second input of the information processing and storage unit 5 (the entry of information is indicated by the dotted arrow in FIG. 1).

Figure 2:
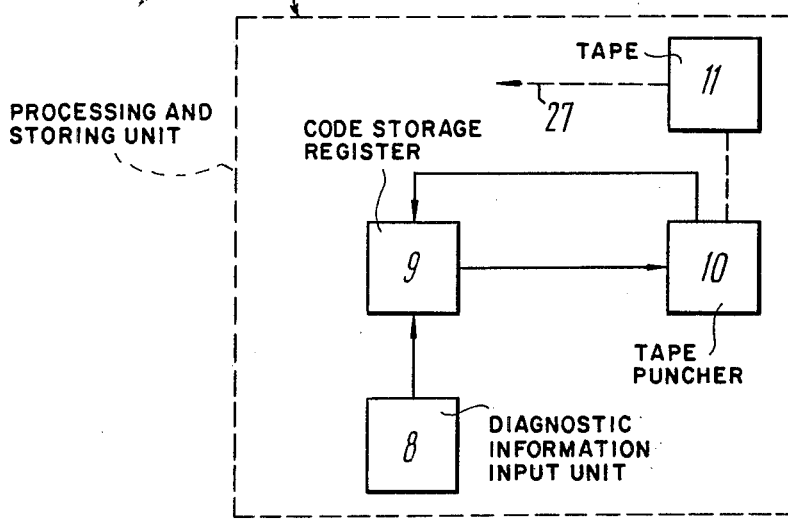
FIG. 2 is a functional diagram of the information processing and storage unit of the apparatus.

The information processing and storage unit 5 comprises a diagnostic information input unit 8 (FIG. 2) and may be a set of push-botton microswitches (not shown), and a code storage register 9 whose first input is connected to an output of the diagnostic information input unit 8.

The information processing and storage unit 5 further includes a tape puncher 10 for punching standard tape 11 which serves to store information. An input of the tape puncher 10 is connected to an output of the code storage register 9, whereas an output of the puncher 10 is connected to a second input of the code storage register 9.

The mechanical beam shifting scanner 3 with the electromechanical unit 4 provided with a drive makes it possible to control the laser beam in the irradiation field and comprises two reflecting elements which are prisms 12 and 13 and mirrors (FIG. 3) respectively adapted for longitudinal and transverse movement in the horizontal plane with the aid of two step motors 14 and 15, two reduction gears 16 and 17, and two carriages 18 and 19, in mutually perpendicular directions.

The mechanical scanner 3 further includes a focusing barrel 20 with a range finder 21.

The barrel 20 is coupled through a reduction gear 22 to a third step electromotor 23 for shifting the directional irradiation in the vertical direction for automatically focusing the beam with the aid of the range finder 21. Mounted on the shafts of the step electromotors 14, 15 and 23 are step counters 24, 25 and 26, respectively.

The control and information readout unit 6 comprises a reading device 27 (FIG. 4) for reading out information from the punched tape 11 perforated in the information processing and storage unit 5. The unit 6 also includes a register 28. Outputs of the reading unit 27 are connected to first inputs of the register 28 and a step counter 29. Entered in the register 28 are codes of instructions on the scanning direction and codes of instructions for controlling operation of the radiation source. Entered in the step counter 29 are codes of instructions on the magnitude of displacement in each coordinate, i.e. the number of steps. Connected to a second input of the step counter 29 is a first OR circuit 30 whose first, second and third inputs are respectively connected to the first, second and third step counters 24, 25 and 26 (FIG. 3) of the electromechanical unit 4. An output of the step counter 29 is connected to an input of a first decoder 31 whose output is connected to a second input of the register 28. The first output of the register 28 is connected via a second OR circuit 32 to the reading device 27. Connected to a third input of the register 28 is a third OR circuit 33. A first input of the third OR circuit 33 is connected to a third input of the step counter 29 and a first output of a control board 34. Second inputs of the second and third OR circuits 32 and 33 are connected to the control system 2 of the radiating source 1. A third input of the second OR circuit 32 is connected to a second output of the control board 34.

A third output of the control board 34 is connected to an input of a pulse generator 35 which is a free-running multivibrator.

The second output of the register 28 is connected to a first input of a second decoder 36 whose second input is connected to a fourth output of the control board 34. First, second, third and fourth outputs of the second decoder 36 are respectively connected to the first inputs of first, second, third and fourth AND circuits 37, 38, 39 and 40. Second inputs of the first, second and third AND circuits 37, 38 and 39 are connected to the output of the pulse generator 35.

Outputs of the first, second and third AND circuits 37, 38 and 39 are respectively connected via electronic commutators 41, 42 and 43 and amplifiers 44, 45 and 46 to the step electromotors 14, 15 and 23 (FIG. 3) of the electromechanical unit 4.

The electronic commutators 41, 42 and 43 are intended to form multiphase voltages for energizing the windings of the step electromotors 14, 15 and 23. A second input and an output of the fourth AND circuit 40, as well as a fifth output of the second decoder 36 are connected to the control system 2 of the radiating source 1.

Practical applications of the apparatus have necessitated the provision of said apparatus with a device for following the position of an object exposed to irradiation in order to ensure spatial adjustment of the laser beam in the course of programmed irradiation in case of an accidental shift in the patient's position.

Figure 4:
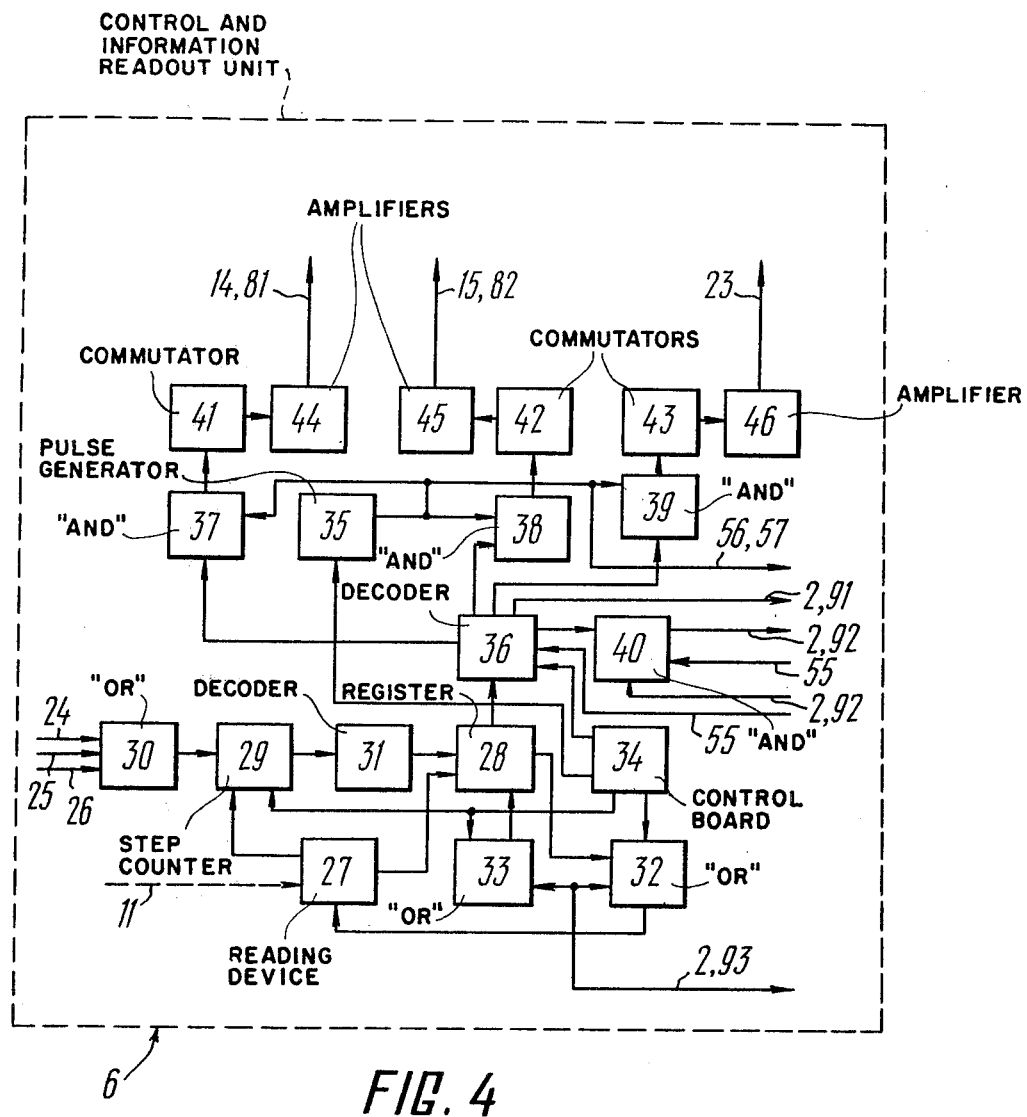
FIG. 4 is a functional diagram of the control and information readout unit.
Figure 5:
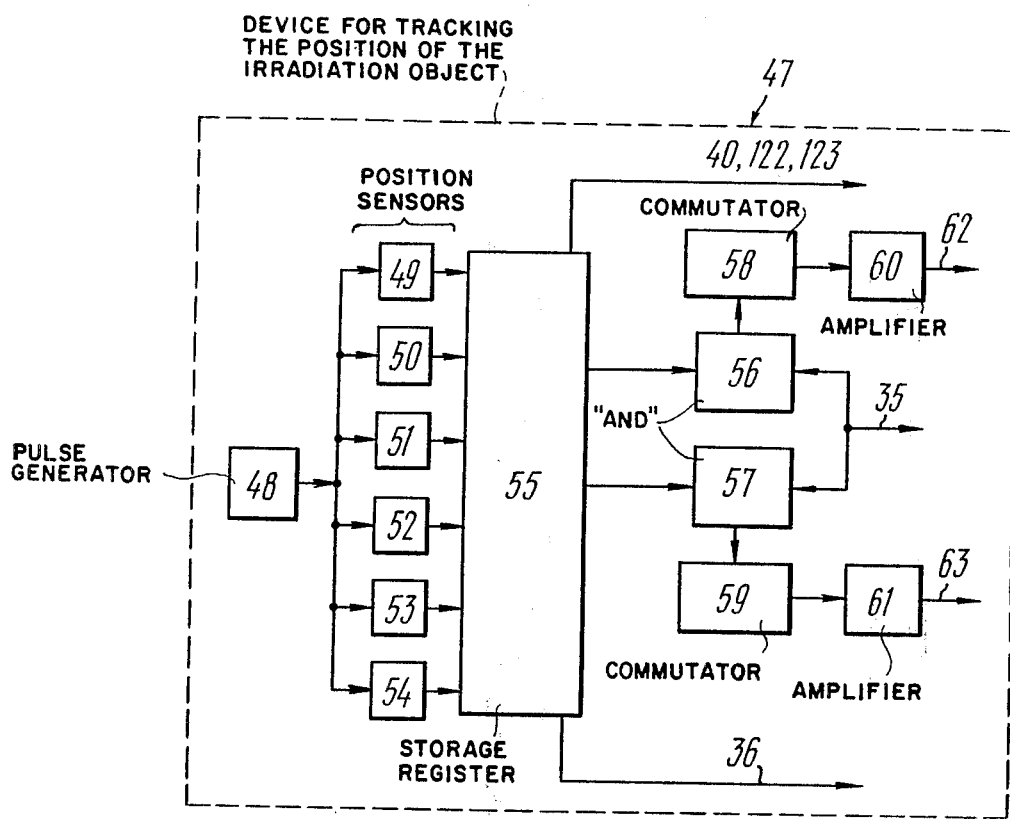
FIG. 5 is a functional diagram of the device for following the location of an irradiation object.

A device 47 for following an irradiation object comprises a pulse generator 48 (FIG. 5) which is a free-running multivibrator whose output is connected to primary windings of position sensors 49, 50, 51, 52, 53 and 54 which are pulse transformers. Secondary windings of said position sensors 49, 50, 51, 52, 53 and 54 are connected to inputs of a storage register 55. First and second outputs of the storage register 55 are respectively connected to the third input of the fourth AND circuit 40 and the third input of the second decoder 36 of the control and information readout unit 6 (FIG. 4). Each third and fourth output of the storage register 55 is respectively connected to a first input of a first AND circuit 56 and a second AND circuit 57. Second inputs of said AND circuits 56 and 57 are connected to the pulse generator 35 of the control and information readout unit 6. Outputs of the AND circuits 56 and 57 are respectively connected to inputs of electronic commutators 58 and 59.

Figure 6:
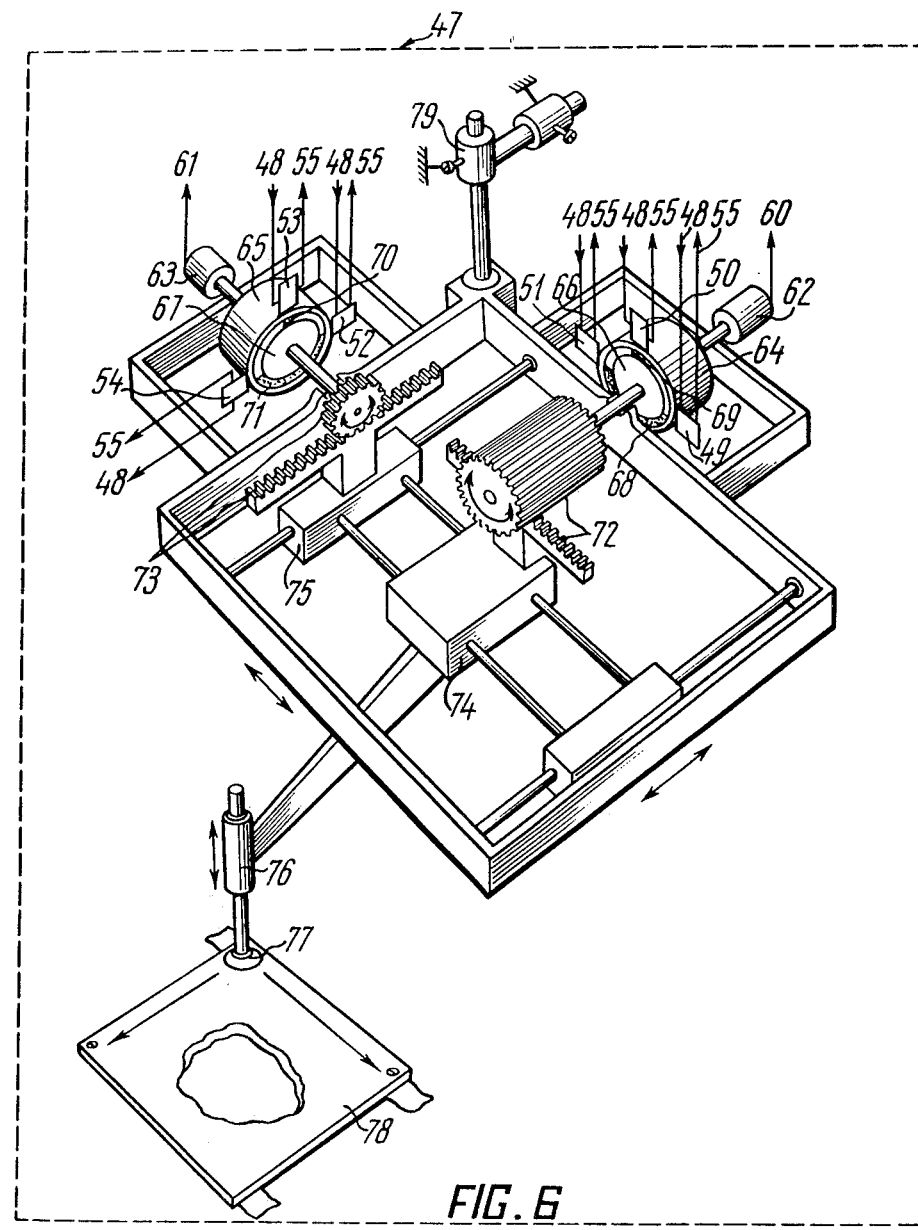
FIG. 6 is electromechanical diagram in perspective of the device for following the location of an irradiation object.

Each of the electronic commutators 58 and 59 is intended for forming multiphase voltages to energize the step electromotors' windings and is connected via amplifiers 60 and 61 to step electromotors 62 and 63 (FIG. 6), respectively. Mechanically coupled to the shaft of each step electromotor 62 and 63 are respective holders 64 and 65 of the position sensors 49, 50, 51, 52, 53 and 54. Coaxially installed in the holders 64 and 65 are movable discs 66 and 67 of a magnetically non-conducting material, each of said discs carrying two ferrite inserts 68, 69 and 70, 71. Said position sensors are so arranged in the holders 64 and 65 that their magnetic circuits interact through an air gap with the ferrite inserts 68, 69 and 70, 71. Each of the discs 66 and 67 is coupled through rack-pinion gears 72 and 73 to carriages 74 and 75. On the carriage 74 there is rigidly mounted one end of a telescopic probe 76 whose second end is attached through a spherical joint 77 to a mask 78 applied onto an irradiation object.

The device 47 for following the position of an irradiation object is also provided with a holder 79 which makes it possible to set the apparatus in the initial position by orienting it with respect to the direction of irradiation.

Figure 7:
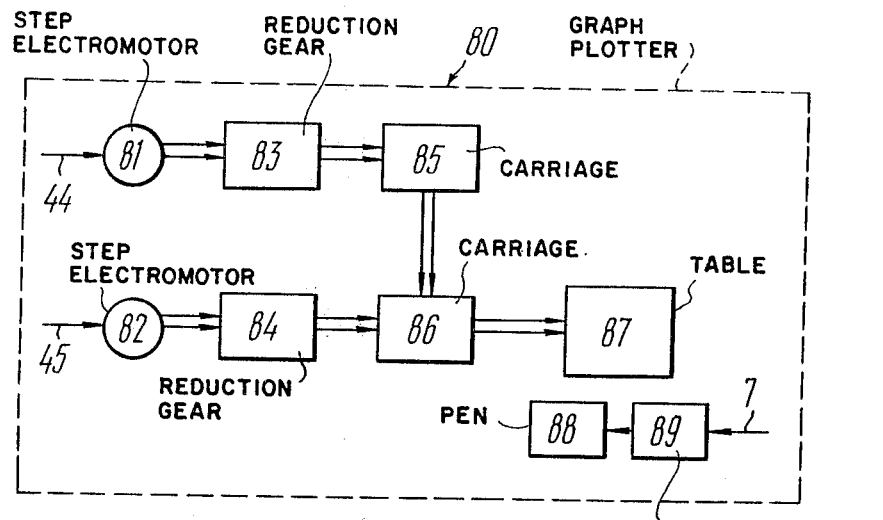
FIG. 7 is a functional diagram of the plotter.

In order to graphically represent the irradiation process, control this process and make it possible for a physician or researcher to compare the irradiation field with orginal diagnostic data, the apparatus of the present invention includes a graph plotter 80 (FIG. 7) which comprises step electromotors 81 and 82 coupled through reduction gears 83 and 84 to carriages 85 and 86 which move a table 87 in two mutually prependicular directions. The plotter 80 is provided with a pen 88 arranged above the table 87 and controlled by an electromagnet 89 connected to the control board 7 (FIG. 1).

Figure 8:
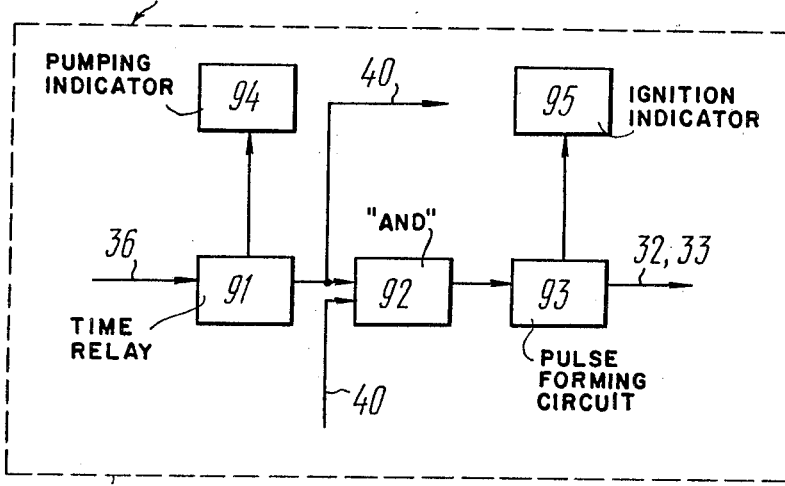
FIG. 8 is a functional diagram of the unit for simulating the operating conditions of the radiation source.

Experience gained in the course of clinical and laboratory tests of the proposed apparatus shows that a physician or researcher must check the irradiation program and reliability of the apparatus prior to irradiation procedure. For this purpose, use should preferably be made of a unit 90 (FIGS. 1 and 8) for simulating the operating conditions of the lasers, whereby simulated scanning of a laser beam is compared to a graphical representation of its movement. One output of the unit 90 for simulating the operating conditions of the radiation source is connected to the information readout unit 6, its input being connected to the control board 7. The unit 90 comprises an electronic time relay 91 (FIG. 8) whose first output is connected to a first input of an AND circuit 92.

An output of the AND circuit 92 is connected to an input of a pulse forming circuit 93. An input of the electronic time relay 91, first and second inputs of the AND circuit 92, and a first output of the pulse forming circuit 93 are respectively connected to the fifth output of the second decoder 36 (FIG. 4), the second input of the fourth AND circuit 40, the output of the fourth AND circuit 40, and the second inputs of the second and third OR circuits 32 and 33 of the control and information readout unit 6.

A second output of the electronic time relay 91 is connected to a pumping indicator 94. A second output of the pulse forming circuit 93 is connected to an ignition indicator 95.

In order to simplify the entry of information and raise the interference immunity of the proposed apparatus, the function of the information processing and storage unit 5 (FIG. 2) and the control and information readout unit 6 may be performed by a photomask readout device 96 (FIG. 9) and a photomask control unit 97 one of whose inputs is connected to an output of the photomask readout device 96, its other input being connected to the control board 7.

The photomask readout device 96 comprises step electromotors 98 and 99 (FIG. 10) coupled through reduction gears 100 and 101 to carriages 102 and 103 which move in two mutually perpendicular directions a table 104 whereon there is mounted a photomask 105. The device 96 further includes a luminous flux source 106 which comprises an electric bulb and a photosensitive element 107 whose function is performed by a photodiode. The motion of the table 104 is restricted by limit switches 108, 109, 110 and 111. The photomask 105 (FIG. 11) is an opaque plate provided with holes.

Figure 9:
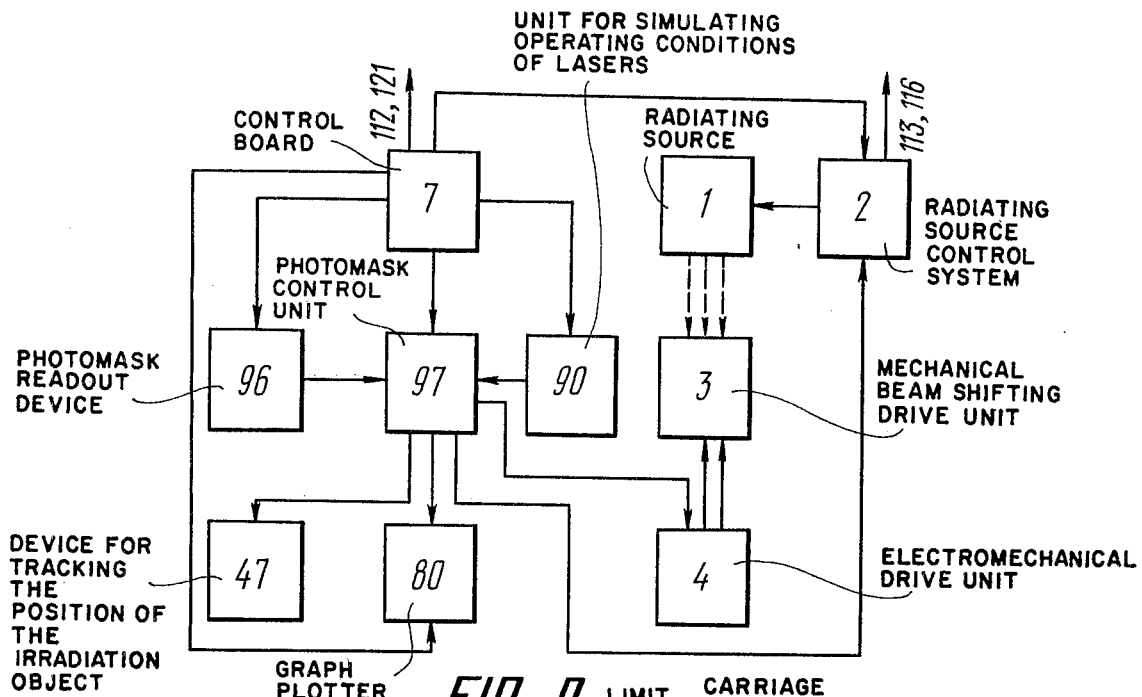
FIG. 9 is a block diagram of a photomask-controlled apparatus.
Figure 10:
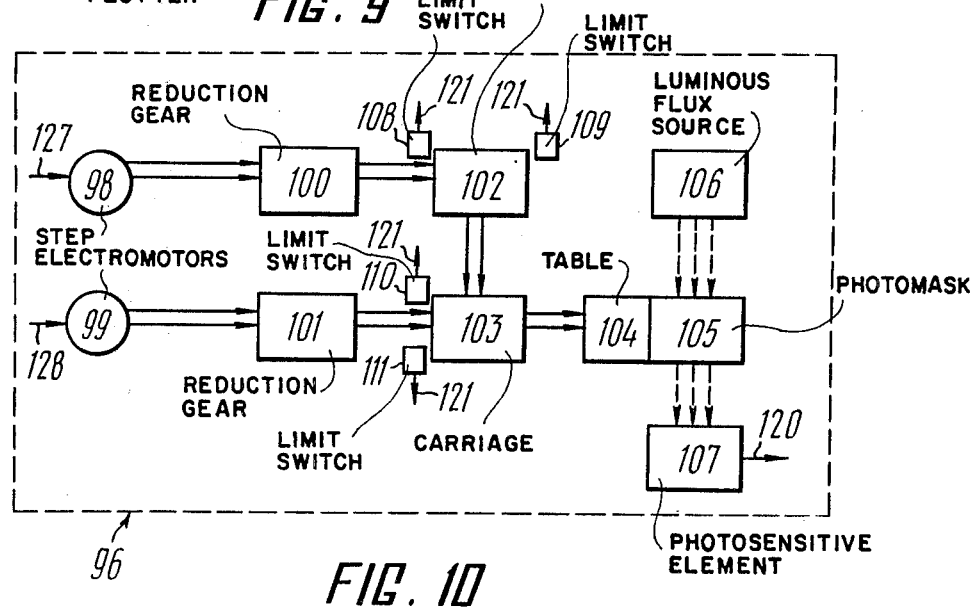
FIG. 10 is a functional diagram of the photomask readout device.
Figure 12:
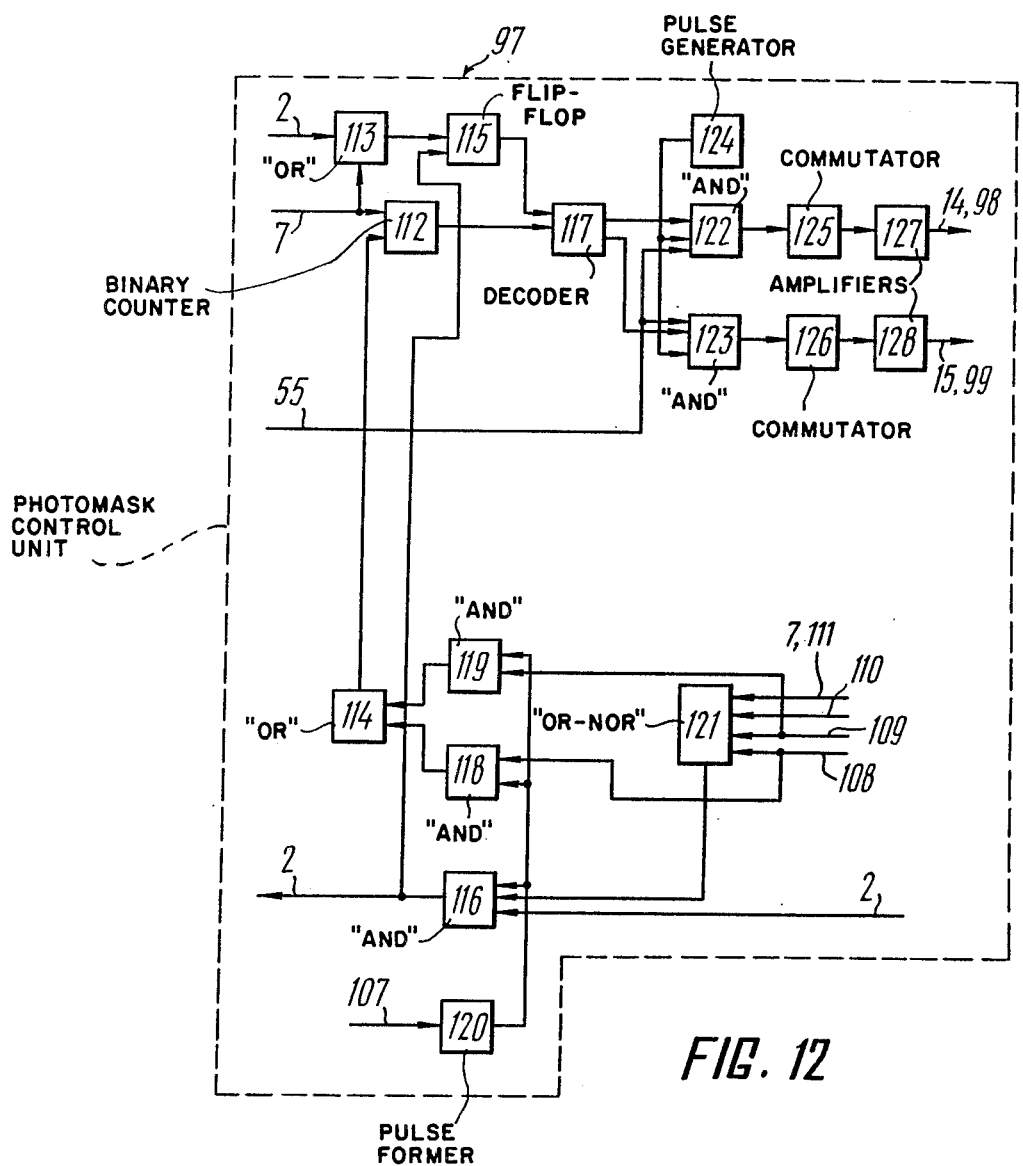
FIG. 12 is a functional diagram of the photomask control unit.

The photomask control unit 97 comprises a binary counter 112 (FIG. 12) one of whose inputs is connected to the control board 7 (FIG. 9) and a first input of a first OR circuit 113; another input of the counter 112 is connected to an output of a second OR circuit 114. A second input of the first OR circuit 113 is connected to the control system 2 of the radiating source 1 (FIG. 9). The unit 97 further includes a flip-flop 115 one of whose inputs is connected to an output of the first OR circuit 113, its other input being connected to an output of a first AND circuit 116 and the control system 2 of the radiating source 1; an output of said flip-flop 115 is connected to a first input of a decoder 117. A second input of the decoder 117 is connected to an output of the counter 112. First inputs of first, second and third AND circuits 116, 118 and 119 are connected to an output of a pulse former 120 whose input is connected to the photosensitive element 107 (FIG. 10), i.e. the photodiode of the photomask readout device 96. Outputs of the second and third AND circuits 118 and 119 are connected to the inputs of the second OR circuit 114. Inputs of an OR-NOR circuit 121 are connected to the limit switches 108, 109, 110 and 111 of the photomask readout device 96 (FIG. 10). A first input of said NOR circuit 121 is connected to the second input of the second AND circuit 118 and the first limit switch 108; a second input of said NOR circuit 121 is connected to the second input of the third AND circuit 119 and the second limit switch 109; a third input of said NOR circuit 121 is connected to the third limit switch 110; a fourth input of the circuit 121 is connected to the fourth limit switch 111 and the control board 7. A first output of the decoder 117 is connected to a first input of a fourth AND circuit 122, its second ouput being connected to a first input of a fifth AND circuit 123. Second inputs of the fourth and fifth AND circuits, 122 and 123, respectively, are connected to the first output of the register 55 (FIG. 5) of the device 47 for following the position of an irradiation object, whereas third inputs of said circuits are connected to an output of a pulse generator 124. Outputs of the fourth and fifth AND circuits 122 and 123 are respectively connected to electronic commutators 125 and 126, amplifiers 127 and 128, and the step electromotors 14 and 15 (FIG. 3) of the electromechanical unit 4 of the scanning device, and to the step electromotors 98 and 99 of the photomask readout device 96 (FIG. 10). The pulse generator 124, the electronic commutators 125 and 126 and the amplifiers 127 and 128 are intended to form multiplase voltages to energize the windings of the step electromotors. An output of the OR-NOR circuit 121 is connected to the second input of the first AND circuit 116 whose third input is connected to the system 2 for controlling the radiating souce 1.

The apparatus of the present invention is operated as follows.

Information is entered through the input unit 8 (FIG. 2) into the code storage register 9 in the form of a parallel binary code. By use of signals from the input unit 8 and the tape puncher 10, the code is readout from the register 9. A code signal is formed, whereby the tape puncher 10 perforates the information storage tape 11. Having punched a row in the tape, the tape puncher 10 initiates a tape transport signal, and the punching cycle is repeated until the entire diagnostic information has been covered. The punched tape is then transferred to the reading unit 27 (FIG. 4) of the control and information readout unit 6.

Prior to the irradiation session, the mask 78 (FIG. 6) is arranged on the irradiation object.

In addition, the device, 47 (FIG. 6) for following the position of the irradiation object is set in initial position corresponding to that of the reference beam.

This is followed by checking the program and operation algorithm of the apparatus from the control board.

At this stage the following operations ar performed: the radiating source 1 (FIG. 1) and its control system 2 are switched off from the control board 7, and the unit 90 for simulating the operating conditions of the radiating source, and the plotter 80 are brought into play. The electromagnet 89 (FIG. 7) of the plotter 80 actuates the pen 88 for graphically representing the information on the irradiation procedure.

From the control board 34 (FIG. 4), the step counter 29 and the register 28 are zeroed (the latter being zeroed via the third OR circuit 33).

The apparatus is brought into action from the control board 34 or 7. As this takes place, the reading unit 27 is actuated via the second OR circuit 32 (FIG. 4), and the punched tape 11 is set in start-stop motion.

Instruction codes from the first four paths of the punched tape 11 are recorded in the register 28 which is used to store the code and deliver it to the second decoder 36.

The second decoder 36 initiates enabling signals for moving the carriages 18 and 19 (FIG. 3) in the horizontal plane, and the barrel 20 with the range finder 21 in the vertical plane; said decoder 36 also initiates signals to control operation of the radiating source ("pump laser" and "ignite laser" signals).

A sequence of pulses (a numeric-frequency code) is removed from the circuits 37, 38 and 39 (FIG. 4).

Figure 3:
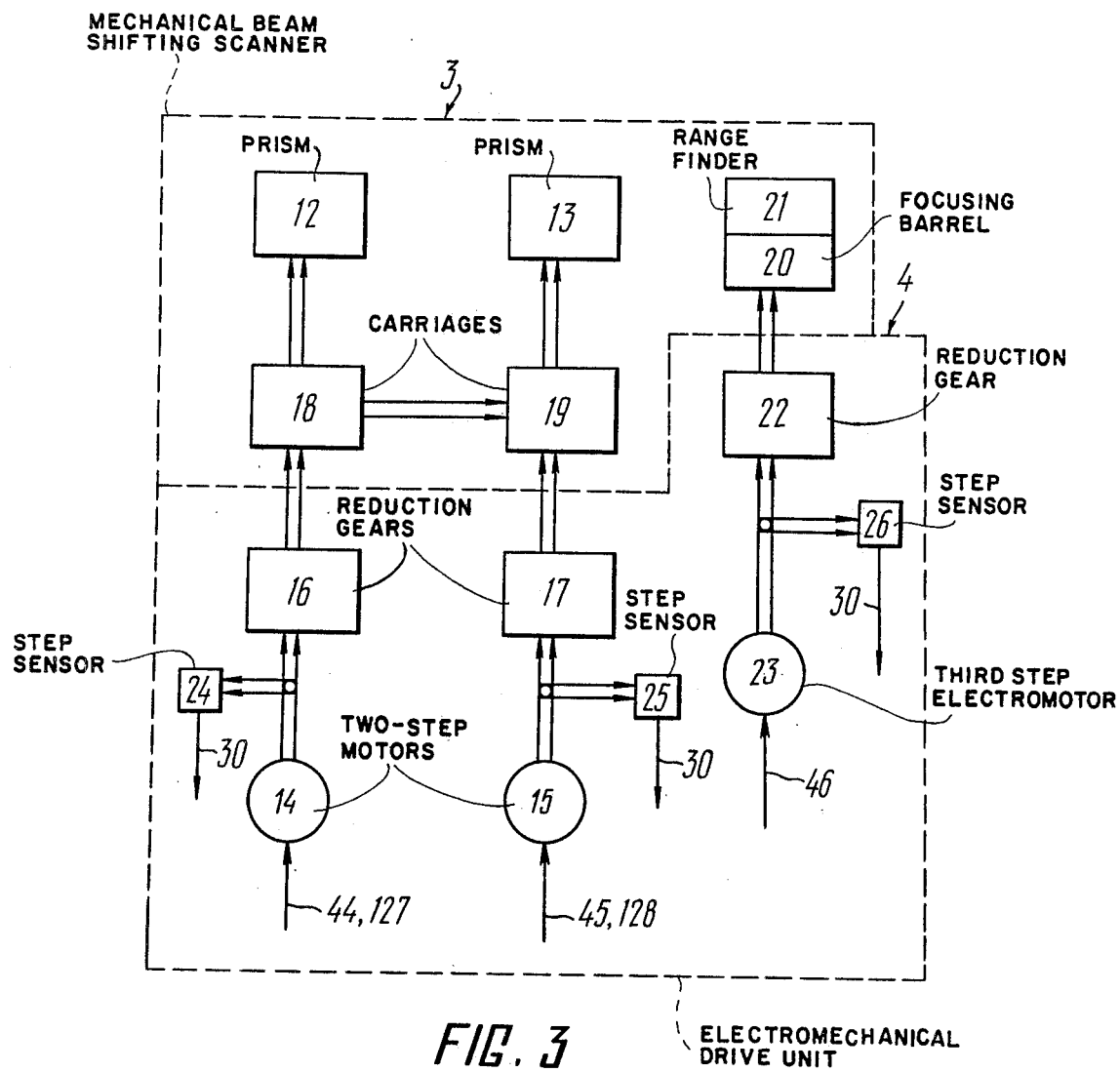
FIG. 3 is a functional diagram of the mechanical and scanning devices and the electromechanical unit of the apparatus.

In executing motion in one of the coordinates in the horizontal plane, for example, of the carriage 18, the sequence of pulses from the AND circuit 37 is applied to the electronic commutator 41 where it is converted into a multi-phase voltage system. From the pulse amplifier 44, said system is applied to the windings of the step electromotor 14 (FIG. 3). Said step electromotor 14 drives the carriage 18 through the reduction gear 16. The carriage 18 moves the prism 12. The number of pulses of the numeric-pulse code determines the number of steps of the step electromotor 14, i.e. the magnitude of total displacement of the prism 12 in the given coordinate; the pulse repetition frequency determines the speed of displacement (scanning) which is set at the control board 34 by switching the RC circuits of the free-running pulse generator 35.

Motion along other coordinates is executed in a similar manner.

In executing motion of the carriage 19 along the other coordinate in the horizontal plane, use is made of the second AND circuit 38 (FIG. 4), the second commutator or electronic switch 42, the second amplifier 45, the second step electromotor 15 (FIG. 3), and the reduction gear 17.

In executing movement of the barrel 20 in the vertical plane, there come into play the third AND circuit 39 (FIG. 4), the third electronic commutator 43, the third amplifier 46, the third step electromotor 23 (FIG. 3), and the reduction gear 22.

Codes of instructions on required magnitudes of displacement of the carriages 18 and 19 and the barrel 20 are entired from the remaining four paths of the punched tape 11 into the binary step counter 29.

The recorded information is transferred in the course of scanning from the step counter 29 via the first OR circuit 30 by pulses removed from the step counters 24, 25 and 26, whereby a pulse is formed after each step of the step electromotors 14, 15 and 23.

The information transfer signal from the counter 29, i.e. the signal on executing required displacement, is applied from the first decoder 31 to the register 28 for the transfer of the code. Following the transfer of the code, the step electromotors 14, 15 and 23 are stopped. The code transfer signal from the register 28 actuates, via the second OR circuit 32, the reading unit 27 for reading information from the tape 11. The tape 11 is again set in start-stop motion. A signal to start pumping is removed from the second decoder 36 and applied to the electronic time relay 91 (FIG. 8) which simulates the charging time of the storage capacitors of the radiation source. The pumping process is checked by the indicator lamp 94. After the electronic relay 91 has been switched off, the indicator lamp 94 goes out, and the pumping over signal is applied to the AND circuit 92 and the fourth AND circuit 40 (FIG. 4).

In executing beam movement in three coordinates and in the case of a shift of the irradiation object, a signal to start ignition is removed from the fourth AND circuit 40 and applied to the second input of the AND circuit 92. A signal from the AND circuit 92 actuates the monostable multivibrator, i.e. the pulse forming circuit 93 which generates an ignition signal which is checked by the indicator lamp 95.

The ignition signal is applied to the control and information readout unit 6 which zeroes via the third OR circuit 33 the register 28 and actuates via the second OR circuit 32 the reading unit 27 for subsequent execution of the irradiation program.

The irradiation area defined by the plotter 80 is compared to the original information, after which the attending physician carries out automatic irradiation.

In the automatic irradiation mode, the control board 7 switches off the operating conditions simulating unit 90 and brings into play the control system 2 of the radiating source 1. Pumping and ignition signals are applied to said control system 2 from the control and information readout unit 6. The system 2 initiates signals to indicate the end of ignition and pumping.

In this mode, the apparatus operates in a manner similar to the one described above.

Automatic irradiation is carried out when the device 47 (FIG. 1) for following the position of the irradiation object applies to the control and information readout unit 6 a signal on the absence of displacement of the irradiation object. As this takes place, the sensors 49, 51 and 52, 54 (FIG. 6) are found at the borderline of the ferrite inserts 68 and 71, and no signals arrive from said sensors; the sensors 50 and 53 are located above the ferrite inserts. From the outputs of the sensors 50 and 53, signals are applied to the register 55 (FIG. 5) which initiates a signal on the absence of a shift of the irradiation object, which signal is applied to the fourth AND circuit 40 (FIG. 4).

Consider now operation of the proposed apparatus for the case when the object exposed to irradiation shifts, for example, in one coordinate. In this case, the telescopic probe 76 (FIG. 6) moves and drives the carriage 74 which turns, through the rack-and-pinion gear 72, the disc 66 with the ferrite inserts 68 and 69. No signal arrives from the sensor 50, whereas from the sensor 49 or 51 (depending upon the direction of the displacement) there is removed a signal which is applied to the register 55. Said register 55 initiates a signal on the displacement of the object of irradiation, which signal is applied to the second decoder 36 to compensate the shift of the object by the respective step electromotor of the electromechanical unit 4 of the scanning device. Simultaneously, there is brought into action the step electromotor 62, which is done through one of the AND circuit 56 and electronic commutator 58 and the amplifer 60. The step electromotor 62 rotates the holder 64 until there is applied a signal from the sensor 49 or 51 to the register 55 which generates a signal on the absence of displacement.

In the automatic irradiation mode, when being controlled by the photomask, the apparatus operates as follows.

The control board 7 switches off the information processing and storage unit 5 (FIG. 1) and the control and information readout unit 6 and actuates the photomask readout device 97 (FIG. 9) and the photomask control unit 97. The luminous flux source 106 (FIG. 10) and the photosensitive element 107 are brought into play. After the mask 78 (FIG. 6) has been arranged on the irradiation object, and after the initial adjustment of the device 47 for following the position of the irradiation object and of the laser beams, and photomask 105 is set in its initial position so that the reference holes A, B and C (FIG. 11) should be found within the irradiation field.

Figure 11:
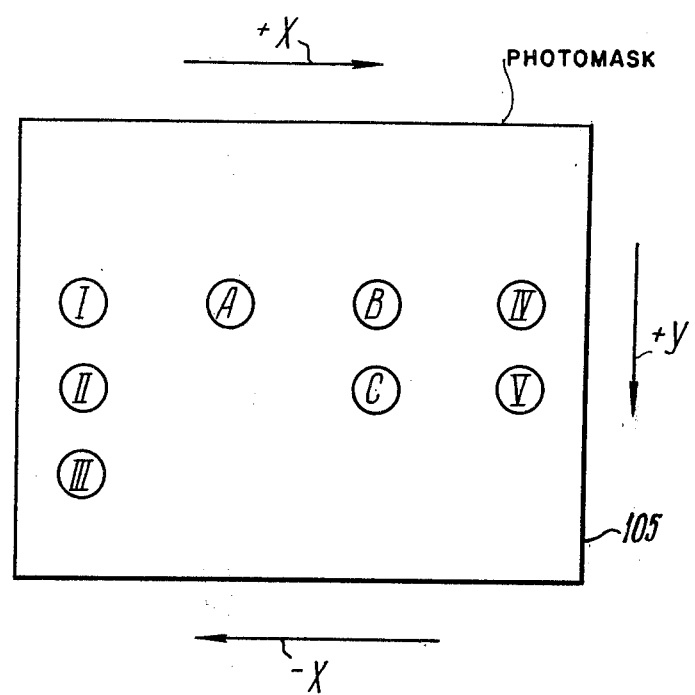
FIG. 11 is a view of a photomask.

The matching is done with the aid of a reference laser beam. The photomask 105 is then placed so that the luminous flux should pass through the reference holes I and II (FIG. 11). The first limit switch 108 is switched on, and therefrom there is applied to the NOR circuit 121 (FIG. 12) a potential which inhibits formation of a signal to ignite the radiating source. As this takes place, the second, third and fourth limit switches, 109, 110 and 111, respectively, are off.

As the apparatus is put into operation, into the counter 112 there is entered information on the movement in the direction +X. This signal passes via the first OR circuit 113 and sets the flip-flop 115 in the digit 1 position, whereby the parallel code is able to arrive from the counter 112 to the decoder 117. At the outputs of the decoder 117, there are produced signals which enable the switching on of the step electromotors of the electromechanical unit 4 of the scanning device (FIG. 9) and the photomask readout device 96, which are switched off when a signal arrives from the device 47 for following the position of the irradiation object on the absence of a shift of the irradiation object.

The photomask 105 moves in the direction +X (FIG. 11). The first limit switch 108 is switched off, ad zero potential is applied therefrom via the NOR circuit 121 to the first AND circuit 116, said signal acting as an enabling signal. As the luminous flux is matched with the hole A, from the photosensitive element 107, following its passage through the pulse former 119, there is applied a signal to the AND circuit 116. If there is applied a signal indicating the end of pumping to the input of this circuit from the control system 2 of the radiating source 1, there is removed from the output of said circuit a signal to start ignition, which signal resets the flip-flop 115. As this takes place, no information is applied from the counter 112 to the decoder 117, and the step electromotors 14, 15 (FIG. 3) and 98, 99 (FIG. 10) are stopped.

A signal indicating the end of ignition of the radiating source 1 sets, via the first OR circuit 113, the flip-flop 115 in the digit 1 position, whereby there are covered the remaining holes of this row.

When the luminous flux is matched with the reference hole IV, signals from the second limit switch 109 and the photosensitive element 107 enter information in the counter 112 on the execution of movement in the direction +Y; simultaneously, to the first AND circuit 116 there is applied a potential which inhibits formation on a signal for igniting the radiating source. As the luminous flux is matched with the reference hole V, in the counter 112 there is entered information on executing movement in the direction —X. The remaining holes of the photomask are covered in a similar manner. As the light flux is matched with the reference hole III, the apparatus is switched off.

What is claimed is:

1. A therapy apparatus comprising a radiating source adapted to generate directional radiation; control means connected to said radiating sources for controlling the radiation parameters of said radiating source; scanner means including electromechanical drive means coupled to said radiating source for focusing a beam of directional radiation such as a laser beam generated by said radiating source on an object to be irradiated and oriented in three spatial coordinates; processing and storing means for receiving, processing and storing information, which contains preselected instructions concerning the desired dosing and directions and extent of movements of said radiating source relative to the boundaries of the object to be irradiated, on a program of exposing biological objects to radiation; and information readout means connected to said processing and storing means for reading out information received by said processing and storing means and for converting the information into electrical signals suitable for controlling the scanning process of the radiating source, said information readout means having a first output connected to an input of said electromechanical drive means and a second output connected to an input of said control means, whereby the orientation and the radiation parameters of the radiation beam generated by said radiating source can be automatically controlled by preselected and programmed instructions.

2. An apparatus as claimed in claim 1, wherein said processing and storing means comprises an information input unit an output of which is connected to a first input of a code storage register, an output of said code storage register being connected to a tape puncher for perforating a tape which serves to store information on irradiation procedure, an output of said tape puncher being connected to a second output of said code storage register.

3. An apparatus as claimed in claim 2, wherein said electromechanical drive means comprises three step electromotors, the first and second electromotors being arranged to shift the beam in the horizontal plane in mutually perpendicular directions, and the third electromotor being arranged to shift the beam in the vertical direction, there being an electromotor step counter mounted on each electromotor's shaft.

4. An apparatus as claimed in claim 3, wherein said information readout means includes a punched tape reading device outputs of which are connected to first inputs of a readout means step counter and a register, there being connected to a second input of said counter a first OR circuit the first, second and third inputs of which are respectively connected to said first, second and third step counters of said step electromotors of said electromechanical drive means, a first decoder the input of which is connected to an output of said readout means step counter and the output of which is connected to a second input of said register a first output of which is connected via a second OR circuit and said reading device, there being connected to a third input of said register a third OR circuit a first input of which is connected to a third input of said readout means step counter and a first output of a control board, second inputs of said second and third OR circuits being connected to said control means for controlling said radiating source, a third input of said second OR circuit being connected to a second output of said control board a third output of which is connected to an input of a pulse generator, a second decoder a first input of which is connected to a second output of said register and a second input of which is connected to a fourth output of said control board, a first AND circuit a first input of which is connected to a first output of said second decoder and a second input of which is connected to the output of said pulse generator, the output of said first AND circuit being connected to an input of a first commutator the output of which is connected to an input of a first amplifier, the output of said first amplifier being connected to windings of said first step electromotor of said electromechanical drive means, a second AND circuit a first input of which is connected to a second output of said second decoder, a second input of said second AND circuit being connected to an output of said pulse generator, the output of said second AND circuit being connected to an input of a second commutator the output of which is connected to an input of a second amplifier the output of which is connected to the windings of said second step electromotor of said electromechanical drive means, a third AND circuit a second input of which is connected to said output of said pulse generator and a first input of which is connected to a third output of said second decoder, the output of said third AND ciircuit being connected to an input of a third commutator the output of which is connected to an input of a third amplifier the output of which is connected to windings of said third step electromotor of said electromechanical drive means, and a fourth AND circuit a first input of which is connected to a fourth output of said second decoder and a second input and an output of said fourth AND circuit, as well as a fifth output of said second decoder are connected to said control means for controlling said radiating source.

5. An apparatus as claimed in claim 4, further comprising a device for following the position of an object exposed to irradiation, comprising a further pulse generator the output of which is connected to a plurality of position sensors the outputs of which are connected to inputs of a code storage register, a first output and a second output of said code storage register being connected to a third input, respectively, of said fourth AND circuit and a third output of said second decoder of said information readout means, third and fourth outputs of said code storage register being connected to first inputs of first and second AND circuits of said following device, respectively, the second inputs of which are connected to said pulse generator of said information readout means, outputs of first and second AND circuits of said following device being connected to respective inputs of electronic commutators coupled via amplifiers to step electromotors which rotate a holder of position sensors, there being installed in said holder a movable disc with ferrite inserts, which disc is coupled by means of a rack-and-pinion gear and carriages moving in the longitudinal and transverse directions to a telescopic probe one end of which is attached to an object exposed to irradiation.

6. An apparatus as claimed in claim 5, further comprising a graph plotter connected to said information readout means and comprising two step electromotors coupled by means of two reduction gears and through two carriages to a movable table above which there is arranged a pen controlled by an electro-magnet from said control board.

7. An apparatus as claimed in claim 6, further comprising a unit for simulating operating conditions of said radiating source which includes a time relay a first output of which is connected to a first input of an AND circuit the output of which is connected to an input of a pulse forming circuit, an input of said time relay, first and second inputs of said AND circuit of said simulating unit and a first output of said pulse forming circuit being respectively connected to a fifth output of said second decoder, a second input of said fourth AND circuit, an output of said fourth AND circuit and second inputs of said second and third OR circuits of said information readout means, second outputs of said time relay and said pulse forming circuit being respectively connected to a pumping indicator and an ignition indicator.

8. An apparatus as claimed in claim 1, wherein the function of said processing and storing means and said information readout means is performed by a photomask readout device and a photomask control unit the input of which is connected to an output of said photomask readout device, which comprises two step electromotors coupled through reduction gears to carriages which move in two mutually perpendicular directions, a movable table whereupon there is placed a photomask, as well as a luminous flux source, a photosensitive element and four limit switches to limit table movement, said photomask control unit comprising a counter a first input of which is connected to a control board and a first input of a first OR circuit, a second input of said counter being connected to an output of a second OR circuit, a second input of said first OR circuit being connected to said control means for controlling said radiating source, an output of said first OR circuit being connected to one input of a flip-flop the other input of which is connected to an output of a first AND circuit and said control means for controlling said radiating source, the output of said flip-flop being connected to a first input of a decoder a second input of which is connected to an output of the counter, first inputs of said first AND circuit, a second AND circuit and a third AND circuit being connected to an output of a pulse former the input of which is connected to said photosensitive element of said photomask readout device, outputs of said second and third AND circuits being connected to inputs of a second OR circuit, a NOR circuit a first input of which is connected to a second input of said second AND circuit and a first limit switch, a second input of said NOR circuit being connected to a second limit switch and a second input of said first AND circuit, a third input of said NOR circuit being connected to a third limit switch, a fourth input of said NOR circuit being connected to an output of said control board and a fourth limit switch, whereas an output of said NOR circuit is connected to a second input of said first AND circuit the third input of which is connected to control means for controlling said radiating source, said first decoder output being coupled to a first input of a fourth AND circuit, a second output of said first decoder being connected to a first input of a fifth AND circuit, second inputs of said fourth and fifth AND circuits being connected to a first register output of a device for following the irradiation object location and third inputs of said fourth and fifth AND circuits being connected to said pulse generator output, each output of said fourth and said fifth AND circuits being connected to an electronic commutator the output of which is coupled via an amplifier to a step motor of said electromechanical drive means of said scanner means and to a step motor of said photomask readout device.

* * * * *